United States Patent [19]

Kawabata

[11] Patent Number: 4,788,315

[45] Date of Patent: Nov. 29, 1988

[54] 2,5-SUBSTITUTED-CYCLOHEXANE-1,4-DIONES AND A PROCESS FOR PRODUCTION THEREOF

[75] Inventor: Takeo Kawabata, Hirakata, Japan

[73] Assignee: Nippon Gohsei Kagaku Kogyo Kabushiki Kaisha, Osaka, Japan

[21] Appl. No.: 91,691

[22] Filed: Sep. 1, 1987

[30] Foreign Application Priority Data

Sep. 3, 1986 [JP] Japan .................................. 61-208276

[51] Int. Cl.$^4$ .................. C07C 121/46; C07C 103/19; C07C 62/20; C07C 69/608
[52] U.S. Cl. .................................... 558/430; 560/126; 562/508; 564/152
[58] Field of Search ...................... 558/430; 560/126; 562/508; 564/152

[56] References Cited

FOREIGN PATENT DOCUMENTS

| 3607275 | 9/1986 | Fed. Rep. of Germany | 560/126 |
|---|---|---|---|
| 7107100 | 2/1971 | Japan | 560/126 |
| 2026259 | 2/1987 | Japan | 558/430 |
| 630886 | 7/1982 | Switzerland | 560/126 |
| 2178034 | 2/1987 | United Kingdom | 558/430 |

OTHER PUBLICATIONS

J. Am. Chem. Soc. 84, (1962) "Substituted Quinodimethans, I. Prep. & Chemistry of 7,7,8,8-Tetracyanoquinodimethan" pp. 3370–3374.
J. Am. Chem. Soc. 84, (1962) "Substituted Quinodimethans, II. Anion-radical Derivatives and Complexes of 7,7,8,8-Tetracyano-quinodimethan" pp. 3374–3387.

Primary Examiner—Joseph Paul Brust
Attorney, Agent, or Firm—Armstrong, Nikaido, Marmelstein & Kubovcik

[57] ABSTRACT

A 2,5-substituted-cyclohexane-1,4-dione of the general formula

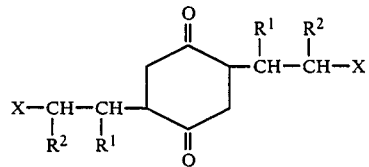

wherein $R^1$ and $R^2$ each is hydrogen or methyl; X is —COOR$^3$ (R$^3$=H or alkyl), —CONR$^4$R$^5$ (R$^4$ and R$^5$ each is hydrogen or alkyl) or —CN and a process for production of the above compound.

8 Claims, No Drawings

2,5-SUBSTITUTED-CYCLOHEXANE-1,4-DIONES AND A PROCESS FOR PRODUCTION THEREOF

BACKGROUND OF THE INVENTION

This invention relates to novel 2,5-substituted-cyclohexane-1,4-diones which are of value as starting materials for the production of polyesters, polyamides, polyurethanes, etc. or for the synthesis of 7,7,8,8-tetracyanoquinodimethane (TCNQ) derivatives.

TCNQ occurs as yellow crystals melting at 293.5° to 296° C. This compound is ready to accept one electron to form a stable anion radical and its derivatives show very small electrical resistance values. These compounds are converted to phenylenedimalonitrile on reduction with thiophenol, mercaptoacetic acid, hydrogen iodide or the like, and the latter is reconverted to TCNQ on oxidation with N-bromosuccinimide. Chemical condensers are among the commercial applications of TCNQ.

Since TCNQ is thus electrically conductive despite its being an organic compound, it is rewarding to discover conductive compounds skeletally analogous to TCNQ for the research and development of organic conductive sbbstances and for their commercial implementation.

This invention is predicated on the discovery of a novel compound in the course of synthetic investigation of various TCNQ derivatives promissing as organic semiconductors.

SUMMARY OF THE INVENTION

The compound of this invention has the following formula, and is a novel compound which has not been described in the literature to this day.

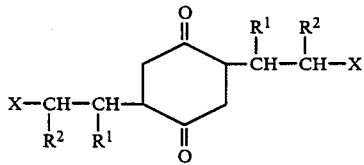

wherein $R^1$ and $R^2$ each is hydrogen or methyl; X is —$COOR^3$ ($R^3$ is hydrogen or alkyl), —$CONR^4R^5$ ($R^4$ and $R^5$ each is hydrogen or alkyl) or —CN.

DETAILED DESCRIPTION OF THE INVENTION

The compound of the above general formula includes the following species, among others.

2,5-Bis(2-carboxyethyl)-cyclohexane-1,4-dione
2,5-Bis[2-(methoxycarbonyl)ethyl]-cyclohexane-1,4-dione
2,5-Bis[2-(ethoxycarbonyl)ethyl]-cyclohexane-1,4-dione
2,5-Bis[2-(butoxycarbonyl)ethyl]-cyclohexane-1,4-dione
2,5-Bis(2-carboxypropyl)-cyclohexane-1,4-dione
2,5-Bis[2-(methoxycarbonyl)propyl]-cyclohexane-1,4-dione
2,5-Bis[2-(ethoxycarbonyl)propyl]-cyclohexane-1,4-dione
2,5-Bis[2-(propoxycarbonyl)propyl]-cyclohexane-1,4-dione
2,5-Bis[2-(hexyloxycarbonyl)propyl]-cyclohexane-1,4-dione
2,5-Bis1-methyl-2-carboxyethyl)-cyclohexane-1,4-dione
2,5-Bis[1-methyl-2-(methoxycarbonyl)ethyl]-cyclohexane-1,4-dione
2,5-Bis[1-methyl-2-(ethoxycarbonyl)ethyl]-cyclohexane-1,4-dione
2,5-Bis[1-methyl-2-(iso-butyloxycarbonyl)ethyl]-cyclohexane-1,4-dione
2,5-Bis(2-cyanoethyl)-cyclohexane-1,4-dione
2,5-Bis(2-cyanopropyl)-cyclohexane-1,4-dione
2,5-Bis[2-(dimethylcarbamoyl)ethyl]-cyclohexane-1,4-dione
2,5-Bis[2-(diethylcarbamoyl)ethyl]-cyclohexane-1,4-dione
2,5-Bis[2-(dimethylcarbamoyl)propyl]-cyclohexane-1,4-dione
2,5-Bis[1-methyl-2-(dimethylcarbamoyl)ethyl]-cyclohexane-1,4-dione The above-mentioned compound can be produced by reacting cyclohexane-1,4-dione with pyrrolidine and reacting the reaction product further with an unsaturated compound of the general formula $CHR^1=CR^2.X$ (wherein $R^1$, $R^2$ and X are as defined hereinbefore).

The above production process can be written as follows.

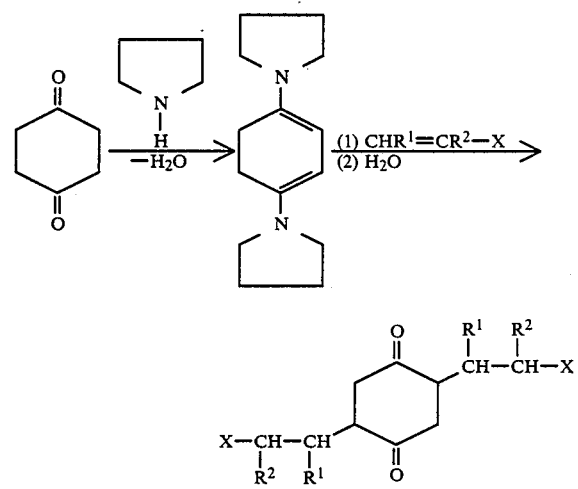

As a first step of the reaction process, cyclohexane-1,4-dione is reacted with pyrrolidine to give a dienamine.

The solvent may for example be benzene, toluene or xylene.

The reaction is preferably conducted under reflux, with byproduct water being constantly removed. While this reaction does not call for the use of a catalyst, p-toluenesulfonic acid or the like may be used as desired.

To prevent oxidation of the product dienamine, it is advantageous to conduct the reaction in a nitrogen gas atmosphere.

The amount of pyrrolidine is selected from the range of 2 to 4 moles per mole of cyclohexane-1,4-dione. The reaction time is preferably in the range of 1 to 3 hours.

After the reaction, the solvent and excess pyrrolidine are removed from the reaction mixture and the product dienamine is reacted with said unsaturated compound.

The solvent for this reaction may for example be dioxane, dimethylformamide, ethanol, methanol, acetonitrile or the like.

The unsaturated compound is used in a proportion of 2 to 4 moles per mole of cyclohexane-1,4-dione.

This reaction is conducted under reflux for about 3 to 24 hours and, after addition of about 2 mole equivalents of water relative to cycloxane-1,4-dione, the reaction is further conducted under reflux for about 1 to 2 hours for hydrolysis to give the desired compound.

After completion of the reaction, the solvent and starting material residues are removed from the reaction mixture, followed by solvent extraction of the desired compound. The solvent is distilled off and the residue of the extract is purified in the routine manner to isolate the desired compound.

The unsaturated compound used in this invention has the general formula of $CHR^1{=}CR^2.X$ and includes such species as acrylic acid, methyl acrylate, ethyl acrylate, methacrylic acid, methyl methacrylate, ethyl methacrylate, crotonic acid, methyl crotonate, ethyl crotonate, acrylonitrile, methacrylonitrile, N,N-dimethyl acrylamide, and so on.

When the substituent group on the product compound is its free form (X=COOH), it is commercially more advantageous to use an unsaturated ester to give an esterification product and, then, hydrolyze it rather than using the corresponding unsaturated acid as a starting material.

The resulting compound is a novel compound which has not been described in the literature and is of commercial value as a starting material for polyesters, polyamides, polyurethanes, etc. and for tetracyanoquinodimethane derivatives.

EXAMPLES

The following examples are further illustrative of this invention.

EXAMPLE 1

2,5-Bis[2-(methoxycarbonyl)ethyl]-cyclohexane-1,4-dione

A mixture of 112 g (1.0 mole) of cyclohexane-1,4-dione, 213 g (3.0 moles) of pyrrolidine and 450 ml of toluene was reacted under reflux in a nitrogen gas stream with by-product water being removed. After 2.5 hours of reaction, the toluene and residual pyrrolidine were removed and 400 ml of dioxane and 258 g (3.0 moles) of methyl acrylate were added.

The reaction was conducted under reflux for 3.5 hours, at the end of which time 100 ml of water was added. The reaction was further continued under reflux for 1 hour. After completion of the reaction, the reaction mixture was cooled and the residual methyl acrylate and dioxane were removed. Then, after addition of 500 ml of water, the mixture was extracted with chloroform.

The chloroform layer was washed with 10% HCl and, then, with water, followed by drying over anhydrous sodium sulfate. The extract was then distilled to remove the solvent, whereupon 207 g of crystals were obtained.

Recrystallization from ether-methanol gave colorless needles. The analytical data are as follows.

Chemical structure:

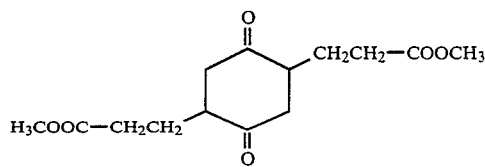

Melting point: 111°–112° C.
IR (KBr) $\nu$: 1740, 1710, 1195, 1175 cm$^{-1}$
NMR (CDCl$_3$) $\delta$: 3.72 (s, 6H), 1.3–3.0 (m, 14H) ppm
MS: M+ 284

EXAMPLE 2

2,5-Bis(2-cyanoethyl)-cyclohexane-1,4-dione

A mixture of 11.2 g (0.1 mole) of cyclohexane-1,4-dione, 21.3 g (0.3 mole) of pyrrolidine and 45 ml of toluene was refluxed for 3 hours in a nitrogen gas stream with by-product water being constantly removed.

After the toluene and residual pyrrolidine were removed, 50 ml of dioxane and 15.9 g (0.3 mole) of acrylonitrile were added and the reaction was conducted under reflux for 12 hours. Then, 5 ml of water was added and the reaction was further continued under reflux for 1 hour.

After completion of the reaction, the reaction mixture was worked up in the same manner as Example 1 to give 10.9 g of crystals. Recrystallization from methanol gave colorless crystals. The analytical data are as follows.

Chemical structure:

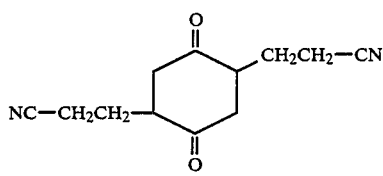

Melting point: 147.8° C.
IR (KBr) $\nu$: 2250, 1710, 1440, 1115 cm$^{-1}$
$^1$H-NMR (DMSO-d$_6$) $\delta$: 1.2–3.3 (m, 14H) ppm
$^{13}$C-NMR (DMSO-d$_6$) $\delta$: 206.9, 120.0, 45.2, 42.8, 25.1, 13.8 ppm
MS: M+ 218

EXAMPLE 3

2,5-Bis[2-(methoxycarbonyl)propyl]-cyclohexane-1,4-dione

Using cyclohexane-1,4-dione, pyrrolidine and methyl methacrylate (30.0 g, 0.3 mole), the procedure of Example 2 was repeated except that benzene was used in lieu of toluene and ethanol in lieu of dioxane to give 14.8 g of oil. Using a Kugel vacuum distillator, the oil was treated at an oven temperature of 190°–210° C. (1.0–1.2 mmHg) to give a colorless viscous oil.

The analytical data are as follows.

Chemical structure:

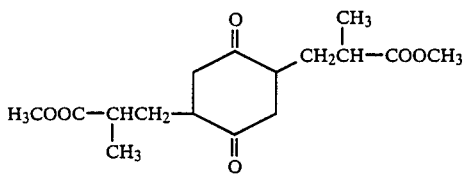

IR (Ge) ν: 2900, 1725, 1435, 1165 cm$^{-1}$
NMR (CDCl$_3$) δ: 3.63 (s, 6H), 3.1–1.7 (m, 12H), 1.17 (d, 6H) ppm
MS: M$^+$ 312

EXAMPLE 4

2,5-Bis[1-methyl-2-(methoxycarbonyl)ethyl]-cyclohexane-1,4-dione

The reaction procedure of Example 3 was repeated except that 30.0 g (0.3 mole) of methyl crotonate was used in lieu of methyl methacrylate to give 12.9 g of oil. This oil was treated in a Kugel distillator at an oven temperature of 180°–190° C. (1.1–1.4 mmHg) to give a viscous oil.

The analytical data are as follows.

Chemical structure:

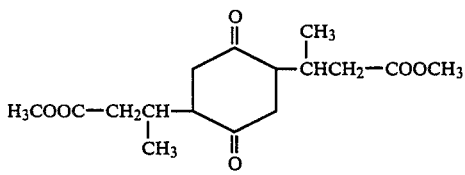

IR (Ge) ν: 2960, 1735, 1715, 1440, 1170 cm$^{-1}$
NMR (CDCl$_3$) δ: 3.64 (s, 6H), 3.1–1.7 (m, 12H), 0.90 (d, 6H) ppm
MS: M$^+$ 312

EXAMPLE 5

2,5-Bis(1-methyl-2-carboxyethyl)-cyclohexane-1,4-dione

In an aqueous medium in the presence of sulfuric acid as the catalyst, 3.0 g of the oil obtained in Example 4 was hydrolyzed under reflux for 8 hours. The procedure gave 2.4 g of crystals.

The analytical data are as follows.

Chemical structure:

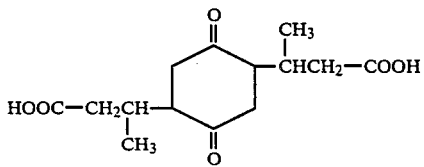

Melting point: 177°–178° C.
IR (KBr) ν: 2500–3500, 1715, 1415, 1295 cm$^{-1}$
NMR (DMSO-d$_6$) δ: 11.97 (s, 2H), 3.1–1.6 (m, 12H), 0.76 (d, 6H) ppm
MS: M$^+$ 284

EXAMPLE 6

2,5-Bis[2-(ethoxycarbonyl)ethyl]-cyclohexane-1,4-dione

A mixture of 11.2 g (0.1 mole) of cyclohexane-1,4-dione, 21.3 g (0.3 mole) of pyrrolidine and 50 ml of toluene was refluxed in a nitrogen gas stream with by product water being constantly removed. After 1.5 hours of reaction, the toluene and residual pyrrolidine were removed and 50 ml of dioxane and 30.0 g (0.3 mole) of ethyl acrylate were added.

The reaction was conducted under reflux for 3.5 hours. Then, after addition of 10 ml of water, the reaction was continued under reflux for an additional hour. After completion of the reaction, the reaction mixture was cooled and the residual ethyl acrylate and dioxane were removed. Then, 100 ml of water was added and the mixture was extracted with ether.

The ether layer was washed with 10% HCl and dried over anhydrous sodium sulfate. Finally, the extract was distilled to remove the ether. The above procedure gave 16.9 g of crystals.

Chemical structure:

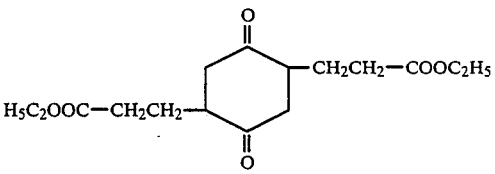

Melting point: 81°–82° C.
IR (KBr) ν: 1735, 1710, 1200 cm$^{-1}$
NMR (CDCl$_3$) δ: 4.8 (q, 4H), 1.3–3.1 (m, 14H) 1.23 (t, 6H) ppm
MS: M$^+$ 312

EXAMPLE 7

2,5-Bis[2-(dimethylcarbamoyl)ethyl]-cyclohexane-1,4-dione

The reaction procedure of Example 1 was repeated except that 297 g (3.0 moles) of N,N-dimethylacrylamide was used in lieu of methyl acrylate to give 72.4 g of crystals. Recrystallization from methanol-acetone gave colorless crystals. The analytical data are as follows.

Chemical structure:

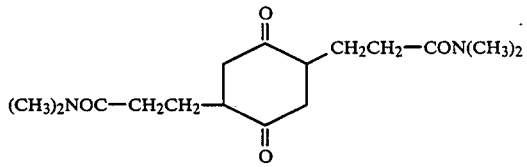

Melting point: 157°–158° C.
IR (KBr) ν: 3050–2800, 1705, 1640, 1500, 1420, 1395, 1340, 1265, 1145 cm$^{-1}$
NMR (CDCl$_3$) δ: 3.03 (s, 6H), 2.95 (s, 6H), 3.2–1.5 (m, 14H) ppm
MS: M$^+$ 310

What is claimed is:
1. A 2,5-bis-substituted-cyclohexane-1,4-dione of the general formula

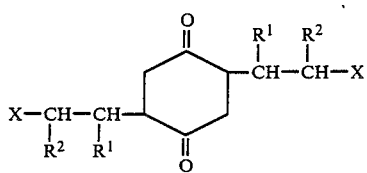

wherein $R^1$ and $R^2$ each is hydrogen or methyl; X is —COOR$^3$ ($R^3$=H or alkyl), —CONR$^4$R$^5$ ($R^4$ and $R^5$ each is hydrogen or alkyl) or —CN.

2. The compound of claim 1 which is 2,5-bis[2-(methoxycarbonyl)ethyl]-cyclohexane-1,4-dione.

3. The compound of claim 1 which is 2,5-bis[2-(methoxycarbonyl)propyl]-cyclohexane-1,4-dione.

4. The compound of claim 1 which is 2,5-bis[2-(ethoxycarbonyl)ethyl]-cyclohexane-1,4-dione.

5. The compound of claim 1 which is 2,5-bis[1-methyl-2-(methoxycarbonyl)ethyl]-cyclohexane-1,4-dione.

6. The compound of claim 1 which is 2,5-bis(1-methyl-2-carboxyethyl)-cyclohexane-1,4-dione.

7. The compound of claim 1 which is 2,5-bis(2-cyanoethyl)-cyclohexane-1,4-dione.

8. The compound of claim 1 which is 2,5-bis[2-(dimethylcarbamoyl)ethyl]-cyclohexane-1,4-dione.

* * * * *